United States Patent
Yang et al.

(10) Patent No.: US 12,367,979 B2
(45) Date of Patent: Jul. 22, 2025

(54) METHOD AND APPARATUS FOR DETERMINING DEMENTIA RISK FACTORS USING DEEP LEARNING

(71) Applicants: THE CATHOLIC UNIVERSITY OF KOREA INDUSTRY—ACADEMIC COOPERATION FOUNDATION, Seoul (KR); GIL MEDICAL CENTER, Incheon (KR); Inha University Research and Business Foundation, Incheon (KR); Min Jeong Wang, Seongnam-si (KR)

(72) Inventors: Dong Won Yang, Seoul (KR); Sang Yun Kim, Seongnam-si (KR); Kee Hyung Park, Incheon (KR); Jee Hyang Jeong, Seoul (KR); Seong Hye Choi, Incheon (KR); Yun Jeong Hong, Uijeongbu-si (KR); Min Jeong Wang, Seongnam-si (KR)

(73) Assignees: THE CATHOLIC UNIVERSITY OF KOREA INDUSTRY-ACADEMIC COOPERATION FOUNDATION, Seoul (KR); Min Jeong Wang, Seongnam-si (KR); GIL MEDICAL CENTER, Incheon (KR); Inha University Research and Business Foundation, Incheon (KR)

( * ) Notice: Subject to any disclaimer, the term of this patent is extended or adjusted under 35 U.S.C. 154(b) by 605 days.

(21) Appl. No.: 17/381,564

(22) Filed: Jul. 21, 2021

(65) Prior Publication Data
US 2023/0023432 A1 Jan. 26, 2023

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/4088* (2013.01); *G06N 3/08* (2013.01); *G16H 10/60* (2018.01); *G16H 15/00* (2018.01)

(58) Field of Classification Search
CPC ........ G16H 50/20; G16H 10/60; G16H 15/00; G16H 40/63; G16H 50/30; A61B 5/4088;
(Continued)

(56) References Cited

U.S. PATENT DOCUMENTS 10,426,400 B2 * 10/2019 Amin ..................... G16H 40/67
10,433,270 B1 * 10/2019 Arab .................. H04W 36/165
(Continued)

FOREIGN PATENT DOCUMENTS

KR 20180072086 * 6/2018
KR 20180072086 A * 6/2018
KR 20220053929 A * 10/2020 ............. G16H 50/30

OTHER PUBLICATIONS

A. Chemparathy et al., "Wearable low-latency sleep stage classifier," 2014 IEEE Biomedical Circuits and Systems Conference (BioCAS) Proceedings, Lausanne, Switzerland, 2014, pp. 592-595, doi: 10.1109/BioCAS.2014.6981795. (Year: 2014).*

*Primary Examiner* — Peter H Choi
*Assistant Examiner* — Sara Jessica Morice De Vargas
(74) *Attorney, Agent, or Firm* — ZION IP; Byungwoong Park

(57) ABSTRACT

There is provided a method for determining dementia risk factors by a server using deep learning. In this instance, the method for determining dementia risk factors includes acquiring biometric information from each subject corresponding to a first control group through a wearable device, acquiring measurement information for each subject corresponding to the first control group, deriving a first dementia risk factor based on the biometric information and the measurement information for each subject, and deriving a (Continued)

second dementia risk factor related to the first dementia risk factor via deep learning performed based on the biometric information related to the first dementia risk factor and control group information.

1 Claim, 11 Drawing Sheets

(51) Int. Cl.
*G06N 3/08* (2023.01)
*G16H 10/60* (2018.01)
*G16H 15/00* (2018.01)

(58) Field of Classification Search
CPC .............. A61B 5/02438; A61B 5/4806; A61B 2560/0242; A61B 5/0004; A61B 5/1118; A61B 5/7267; A61B 5/0042; A61B 5/055; A61B 5/369; G06N 3/08
USPC ........................................................... 705/3
See application file for complete search history.

(56) References Cited

U.S. PATENT DOCUMENTS

| | | |
|---|---|---|
| 2007/0299360 A1 | 12/2007 | Snyder et al. |
| 2015/0073025 A1* | 3/2015 | Roses |
| 2017/0039324 A1* | 2/2017 | Francois ................ G16H 10/60 |
| 2018/0068083 A1* | 3/2018 | Cohen .................... G16H 50/20 |
| 2020/0260977 A1* | 8/2020 | Kang ..................... G16H 50/50 |
| 2022/0022790 A1* | 1/2022 | Kim ....................... G06T 7/0012 |
| 2022/0412994 A1* | 12/2022 | Innocenzi .......... G01N 33/9406 |

\* cited by examiner

METHOD AND APPARATUS FOR DETERMINING DEMENTIA RISK FACTORS USING DEEP LEARNING

FIELD

The present disclosure relates to a method and apparatus for determining dementia risk factors using deep learning. More particularly, the present disclosure relates to a method for deriving dementia risk factors using hospital measurement information and biometric information measured by a wearable device.

BACKGROUND

With the growing social concerns about dementia, there are increasing studies to identify the cause of dementia and verify dementia related risk factors. Dementia may be a brain disorder that occur with aging. In this instance, dementia may gradually cause memory loss. Additionally, dementia may include changes in personality or cognitive decline.

Dementia may disrupt daily life, and long-term decline in brain function in even normal people may lead to the development of dementia. To prevent dementia, it is necessary to analyze the cause of dementia and dementia related risk factors.

In general, medical methods such as brain images or biomarkers may be used to diagnose dementia. Additionally, for example, physical activity such as regular exercise or regular sleep may develop or mitigate dementia symptoms.

When considering the above description, in addition to the medical methods for identifying dementia symptoms, it may be necessary to identify risk factors related to dementia to prevent and treat dementia, and a method using deep learning will be described below.

SUMMARY

The present disclosure is directed to providing a method and apparatus for determining dementia risk factors using deep learning.

The present disclosure is directed to providing a method for deriving dementia risk factors using hospital measurement information and biometric information measured by a wearable device.

The present disclosure is directed to providing a method for deriving a new dementia risk factor using a dementia risk factor.

According to an embodiment of the present disclosure, there is provided a method for determining dementia risk factors by a server using deep learning. In this instance, the method for determining dementia risk factors includes acquiring biometric information from each subject corresponding to a first control group through a wearable device, acquiring measurement information for each subject corresponding to the first control group, deriving a first dementia risk factor based on the biometric information and the measurement information for each subject, and deriving a second dementia risk factor related to the first dementia risk factor via deep learning performed based on the biometric information related to the first dementia risk factor and control group information.

Additionally, according to an embodiment of the present disclosure, there is provided a server for determining dementia risk factors using deep learning. In this instance, the server includes a transmitting/receiving unit to transmit and receive a signal, a deep learning training unit to train deep learning, and a control unit to control the transmitting/receiving unit and the deep learning training unit. In this instance, the control unit may acquire biometric information from each subject corresponding to a first control group through a wearable device, acquire measurement information for each subject corresponding to the first control group, derive a first dementia risk factor based on the biometric information and the measurement information for each subject, and derive a second dementia risk factor related to the first dementia risk factor via deep learning performed based on the biometric information related to the first dementia risk factor and control group information.

Additionally, according to an embodiment of the present disclosure, there is provided a system for determining dementia risk factors. In this instance, the system includes a server to determine a dementia risk factor via deep learning, and a wearable device to measure biometric information, and an Internet of Things (IoT) device to measure the wearable device and the biometric information together, or transmit the measured biometric information to the server. In this instance, the server may acquire the biometric information from the wearable devices of each subject corresponding to a first control group, acquire measurement information for each subject corresponding to the first control group, derive a first dementia risk factor based on the biometric information and the measurement information for each subject, and derive a second dementia risk factor related to the first dementia risk factor via deep learning performed based on the biometric information related to the first dementia risk factor and control group information.

Additionally, the following features may be applied in common to the method, device, server and system for deriving dementia risk factors.

According to an embodiment of the present disclosure, in case that the deep learning for deriving the second dementia risk factor is performed, a second control group may be further set, the biometric information related to the first dementia risk factor may include the biometric information acquired from each subject corresponding to the first control group and biometric information acquired from each subject corresponding to the second control group, and the deep learning may be performed through comparison between the biometric information of the first control group and the biometric information of the second control group.

Additionally, according to an embodiment of the present disclosure, the first control group may be a control group corresponding to a subjective cognitive impairment state, and the second control group may be a control group corresponding to a normal state.

Additionally, according to an embodiment of the present disclosure, the biometric information may be acquired further using an IoT device.

Additionally, according to an embodiment of the present disclosure, the measurement information may be derived based on at least one of brain imaging, computed tomography (CT), magnetic resonance imaging (MRI), electroencephalogram (EEG) or medical findings data.

Additionally, according to an embodiment of the present disclosure, in case that the first dementia risk factor is derived based on the biometric information and the measurement information for each subject, the biometric information and the measurement information may be transmitted from the server to a medical institution, and the server may receive first dementia risk factor information determined by the medical institution.

Additionally, according to an embodiment of the present disclosure, in case that the first dementia risk factor is derived based on the biometric information and the measurement information for each subject, the server may perform deep learning based on the biometric information and the measurement information, and first dementia risk factor information may be directly acquired through the server based on the deep learning.

The present disclosure may provide a method and apparatus for determining dementia risk factors using deep learning.

The present disclosure may provide a method for deriving dementia risk factors using hospital measurement information and biometric information measured by a wearable device.

The present disclosure may provide a method for deriving a new dementia risk factor using a dementia risk factor.

The effect that may be obtained from the present disclosure is not limited to the above-mentioned effects, and another effect not mentioned herein will be clearly understood by those having ordinary skill in the technical field pertaining to the present disclosure from the following description.

DETAILED DESCRIPTION OF THE EMBODIMENTS

Hereinafter, the preferred embodiments according to the present disclosure are described in detail with reference to the accompanying drawings. The detailed description that will be disclosed below is provided to describe exemplary embodiments of the present disclosure together with the accompanying drawings, but not intended to describe an only embodiment for practicing the present disclosure. The following detailed description includes details to provide a full and thorough understanding of the present disclosure. However, those skilled in the art understand that the present disclosure may be embodied without such details.

The following embodiments include the elements and features of the present disclosure in any combination. Unless expressly stated otherwise, each element or feature may be considered optional. Each element or feature may be embodied in non-combination with another element or feature. Additionally, the embodiments of the present disclosure may include some elements and/or features in combination. The order of the operations described in the embodiments of the present disclosure may be subject to change. Some elements or features in an embodiment may be included in another embodiment or replaced with corresponding elements or features of another embodiment.

Particular terms as used herein are provided to help the understanding of the present disclosure, and the use of the particular terms may be changed to other forms without departing from the technical spirit of the present disclosure.

In some cases, to avoid ambiguities in the concept of the present disclosure, well-known structures and devices are omitted, or each structure and device are illustrated in the form of a block diagram with the essential functions. Additionally, like elements are described using like reference signs throughout the specification.

Additionally, the term first and/or second as used herein may be used to describe a variety of elements, but the elements should not be limited by the terms. These terms are used to distinguish an element from another, and for example, a first element may be referred to as a second element, and likewise, a second element may be referred to as a first element without departing from the scope of protection according to the concept of the present disclosure.

Additionally, unless expressly stated to the contrary, "comprise" when used in this specification, specifies the presence of stated elements but does not preclude the presence or addition of one or more other elements. Additionally, the term "unit" as used herein refers to a processing unit of at least one function or operation, and this may be implemented as a combination of hardware and/or software.

Figure 1A:
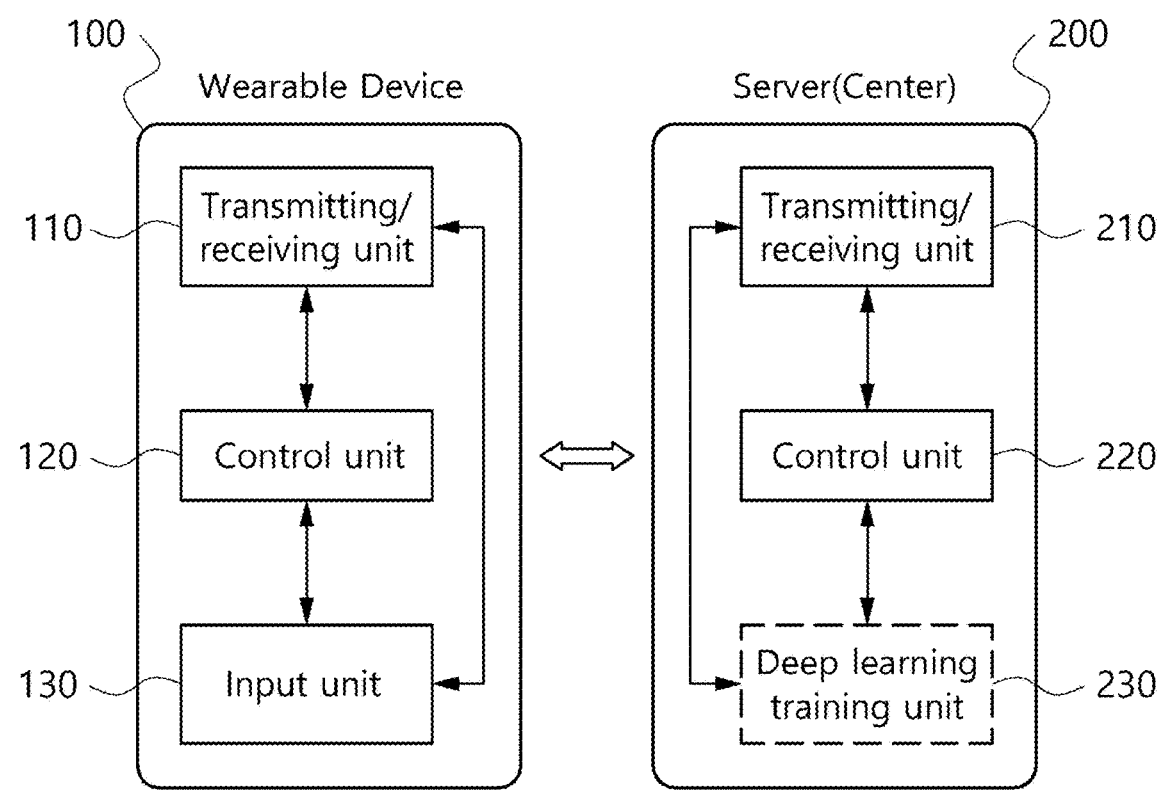
FIG. 1A is a diagram showing a wearable device, a server and an Internet of Things (IoT) device according to an embodiment of the present disclosure.
Figure 1B:
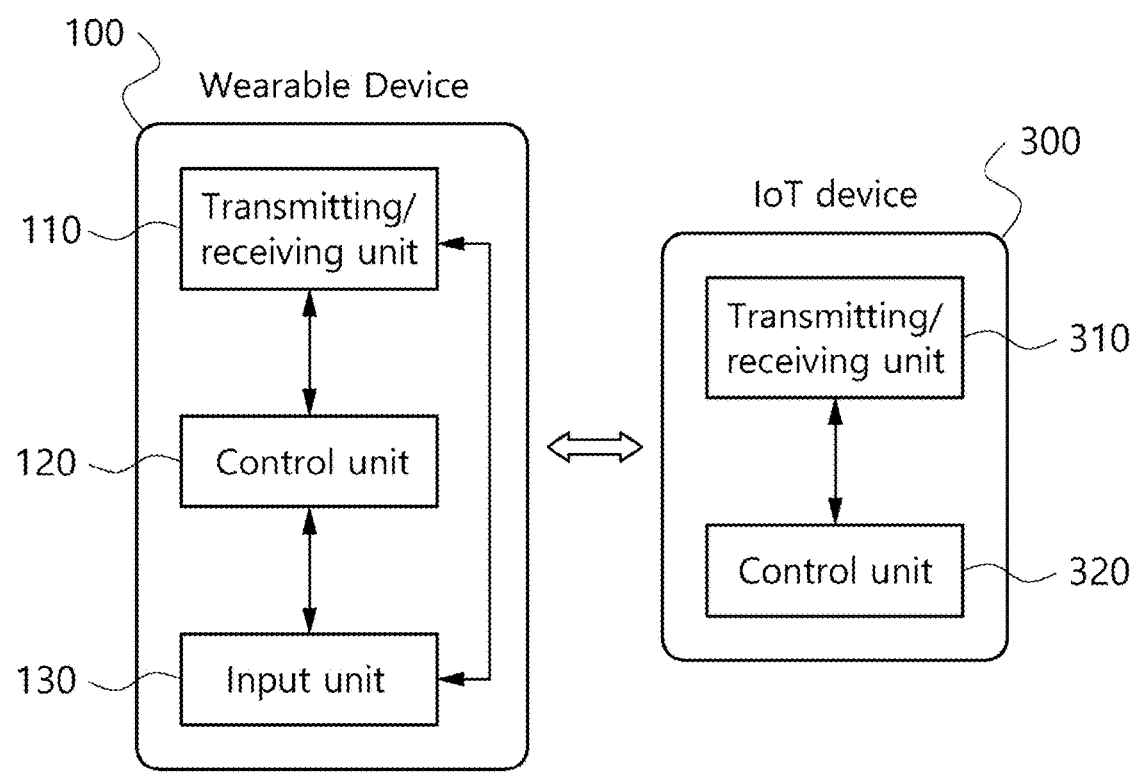
FIG. 1B is a diagram showing a wearable device, a server and an Internet of Things (IoT) device according to an embodiment of the present disclosure.

FIGS. 1A and 1B are diagrams showing a wearable device, a server and an Internet of Things (IoT) device according to an embodiment of the present disclosure. Referring to FIG. 1A, the wearable device 100 may include a transmitting/receiving unit 110, a control unit 120 and an input unit 130. Additionally, for example, the wearable device 100 may further include any other component, and is not limited to the above-described embodiment.

For example, the transmitting/receiving unit 110 may be configured to transmit and receive a signal to/from other device. For example, the other device may be a server (or a center) 200. Additionally, the other device may be an IoT device or a smartphone. That is, the other device may be a device with whom the wearable device 100 can exchange a signal, and is not limited to a particular device.

For example, the control unit 120 may be configured to control the transmitting/receiving unit 110 and the input unit 130. Additionally, the control unit 120 may be further configured to control other components, and is not limited to the above-described embodiment.

Additionally, the input unit 130 may be configured to acquire a biosignal. For example, the input unit 130 may acquire the biosignal through at least one of a location sensor, an acceleration sensor, a motion sensor or any other sensor. That is, the input unit 130 may configured to acquire or sense an external signal, and is not limited to the above-described embodiment.

Additionally, the server (or the center) 200 may include a transmitting/receiving unit 210 and a control unit 220. Additionally, the server 200 may further include a deep learning training unit 230, and may further include any other component.

For example, the transmitting/receiving unit 210 may be configured to transmit and receive a signal to/from other device. For example, the other device may be the wearable device 100. Additionally, the other device may be an IoT device or a smartphone. That is, the other device may be a device with whom the server 200 can exchange a signal, and is not limited to a particular device.

For example, the control unit 220 may be configured to control the transmitting/receiving unit 210 and the deep learning training unit 230. Additionally, the control unit 220 may be further configured to control other components, and is not limited to the above-described embodiment.

The deep learning training unit 230 may perform deep learning through biometric information acquired from the wearable device 100 and other information and derive dementia risk factors based on a learning model. For example, the dementia risk factors may be derived through the biometric information acquired from the wearable device 100 and measurement information. In this instance, for example, the measurement information may be information measured through brain imaging, computed tomography (CT), magnetic resonance imaging (MRI) and electroencephalogram (EEG), and it will be described below.

Additionally, referring to FIG. 1B, the wearable device 100 may exchange a signal with the IoT device 300. That is, the wearable device 100 may communicate with the IoT device 300. In this instance, for example, the IoT device 300 may include a component for communication. For example, the IoT device 300 may include a transmitting/receiving unit 310 and a control unit 320. In this instance, for example, the transmitting/receiving unit 310 may communicate with the wearable device 100 or the server 200. Additionally, for example, the transmitting/receiving unit 310 may communicate with any other device, and there is no limitation on the type of device. Additionally, the control unit 320 may be configured to control the components in the IoT device 300. In another example, the IoT device 300 may be a low power device. The IoT device 300 may be a low power device which only transmits a particular signal, and is not limited to the above-described embodiment. Additionally, for example, the IoT device 300 may be a device that operates based on an IoT cloud. For example, the IoT device 300 may be a device fixed and installed at a specific location. In a more specific example, the IoT device 300 may receive a signal from the wearable device 100, and transmit data to the server or other device through the IoT cloud, and is not limited to the above-described embodiment. Additionally, for example, the IoT device 300 may provide necessary information when the wearable device 100 measures the biosignal, and it will be described below.

Figure 2:
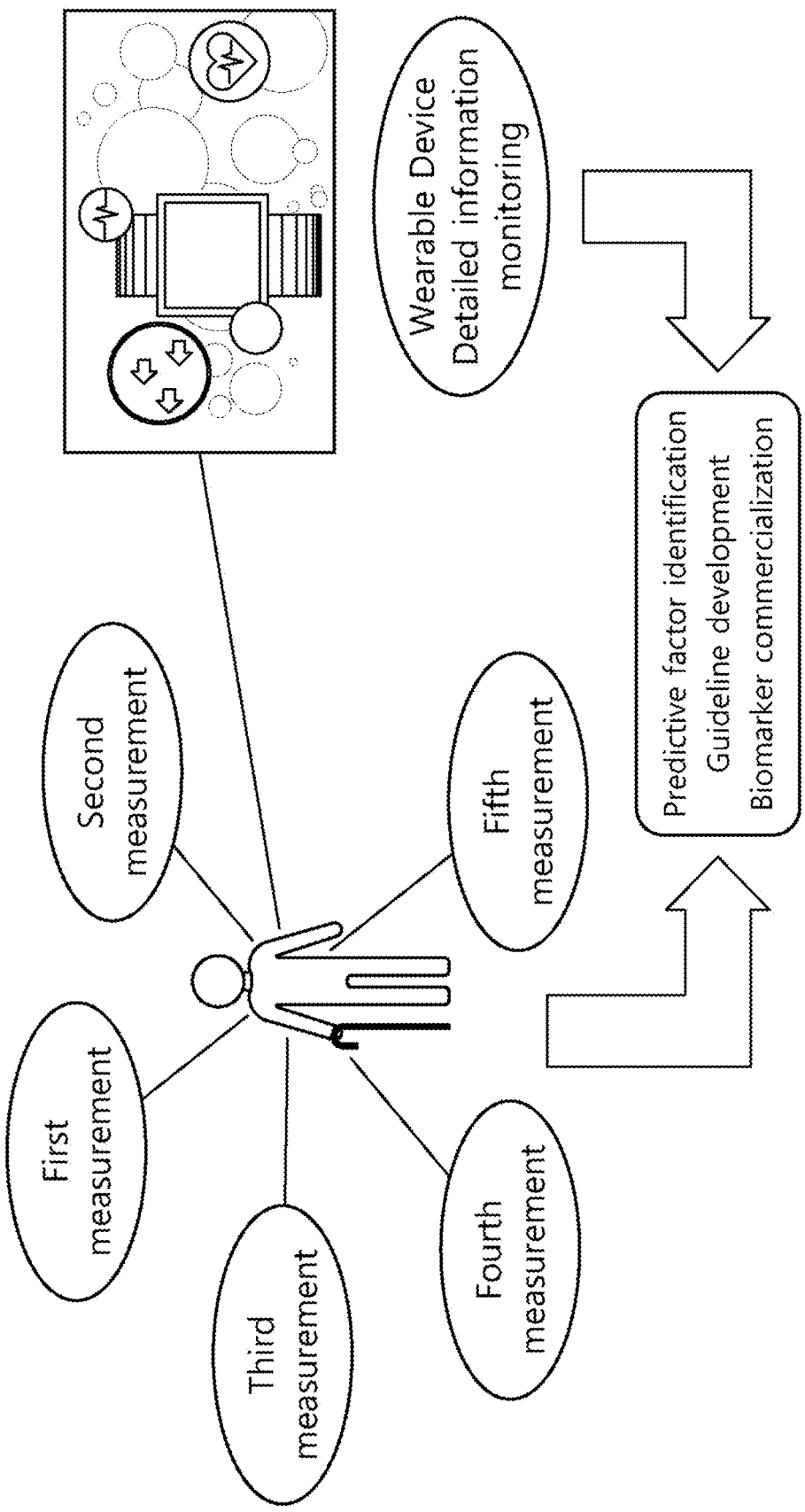
FIG. 2 is a diagram showing a method for deriving dementia risk factors according to an embodiment of the present disclosure.

FIG. 2 is a diagram showing a method for deriving dementia risk factors according to an embodiment of the present disclosure. Referring to FIG. 2, dementia related information may be acquired through various measurements.

For example, the measurements may be brain imaging, CT, MRI or EEG measurements. Additionally, for example, the measurements may refer to measurements made through Amyloid positron emission tomography (PET). In another example, the measurements may refer to measurements through blood biomarkers. In still another example, the measurements may refer to measurements performed through doctors such as screening questionnaire or clinical findings.

That is, the measurements may refer to acquisition of information about the presence or absence of dementia or the likelihood of developing dementia through a variety of methods, and the acquired information may be the measurement information. For example, the measurement information may be information acquired by measuring through hospitals or other medical institutions. In this instance, for example, dementia severity may be measured according to the measurement information.

For example, the dementia severity may be measured as mild cognitive impairment stage according to the measurement information. Additionally, Alzheimer's disease may be measured according to the measurement information. In another example, the dementia severity may be measured as subjective cognitive impairment stage where dementia worsens. That is, each stage may be determined based on dementia progression as the presence or absence of dementia or the likelihood of developing dementia through the above-described measurements. For example, hereinafter, for convenience of description, each stage of dementia is indicated by number. In this instance, for example, the second stage may define more severe dementia than the first stage, and the third stage may define more severe dementia than the second stage. In this instance, the above-described stages are provided for convenience of description, and are not limited to the above-described stages. For example, the subjective cognitive impairment stage may be the first stage, and the mild cognitive impairment stage may be the second stage. This is provided for illustrative purposes and not intended thereto.

Figure 3:
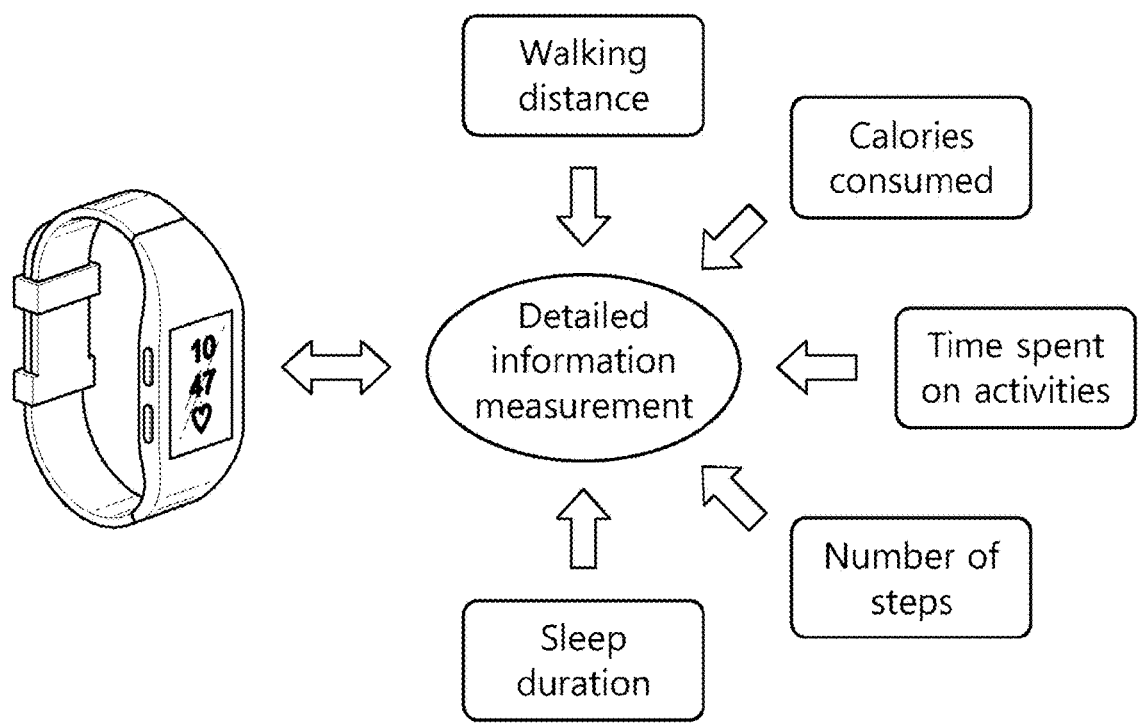
FIG. 3 is a diagram showing a method for measuring biometric information by a wearable device according to an embodiment of the present disclosure.

FIG. 3 is a diagram showing a method for measuring biometric information by the wearable device according to an embodiment of the present disclosure. Meanwhile, referring to FIG. 3, the stages may be determined according to dementia progression through the above-described measurement information. In this instance, for example, biometric information of subjects for the measurement information may be measured. For example, the biometric information may be a variety of physical information. In a more specific example, the physical information may be at least one of calories consumed, time spent on activities, sleep duration, the type of sleep for each sleep time, the heart rate, the number of steps, the walking distance or the number of exercises. Additionally, the physical information may be a variety of information measured through any other wearable device, and is not limited to the above-described embodiment. That is, the biometric information may be information acquired from the subject through the wearable device, and is not limited to the above-described embodiment.

Figure 4:
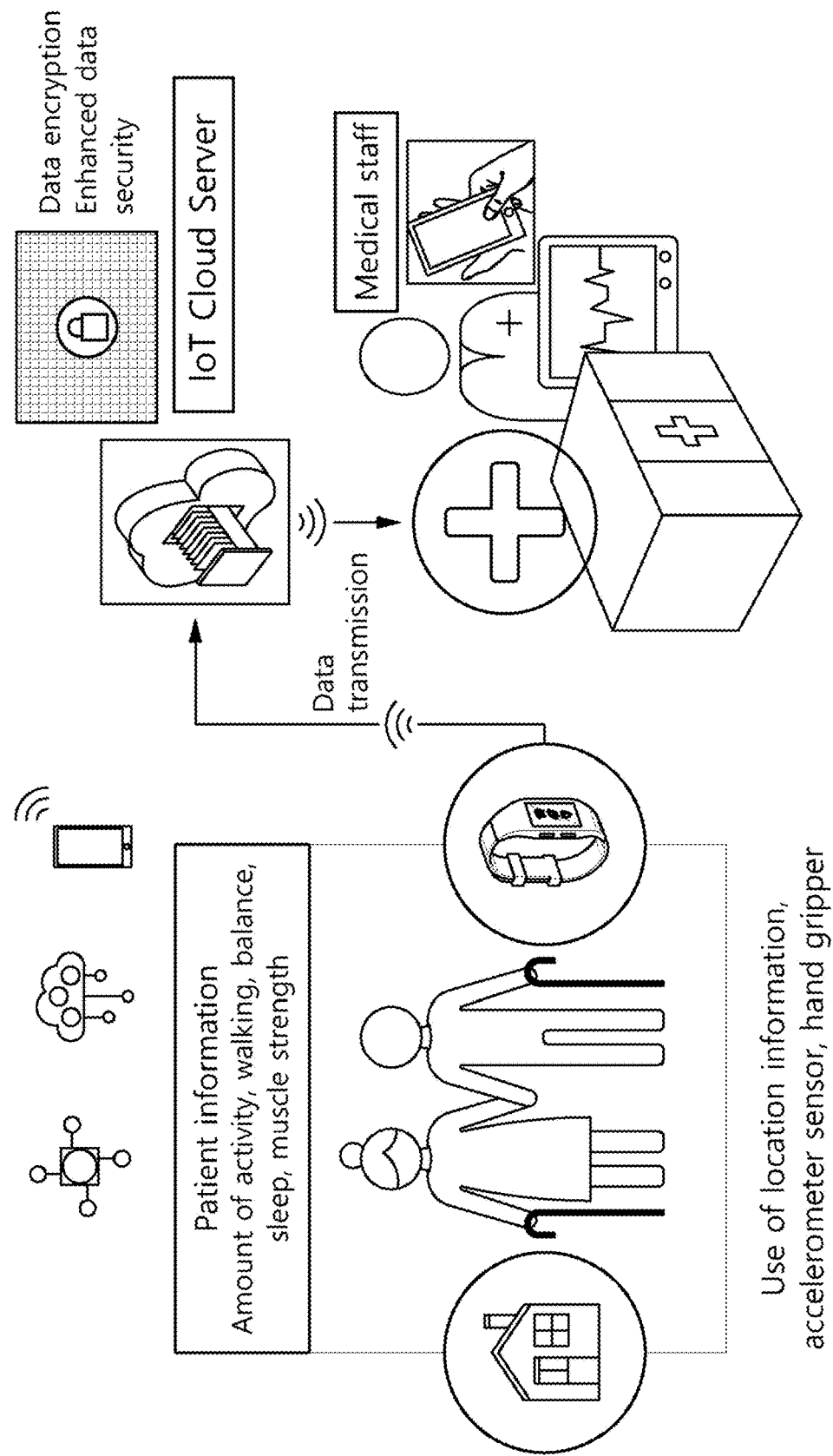
FIG. 4 is a diagram showing a method for identifying dementia risk factors using biometric information according to an embodiment of the present disclosure.

FIG. 4 is a diagram showing a method for identifying dementia risk factors using biometric information according to an embodiment of the present disclosure. In this instance, for example, the server (or the center) may estimate the dementia risk factor for developing dementia using the biometric information acquired through the wearable device and the above-described measurement information. In this instance, for example, the dementia risk factor may be estimated by a person (e.g. a medical staff) based on the biometric information and the measurement information.

In another example, the dementia risk factor may be derived through statistical information generated through the biometric information acquired from the server and the measurement information. Additionally, for example, the dementia risk factor may be derived via deep learning through the biometric information acquired from the server and the measurement information, and is not limited to the above-described embodiment. In this instance, for example, a new dementia risk factor may be derived via deep learning through the dementia risk factor derived as described above, and it will be described below.

Figure 5:
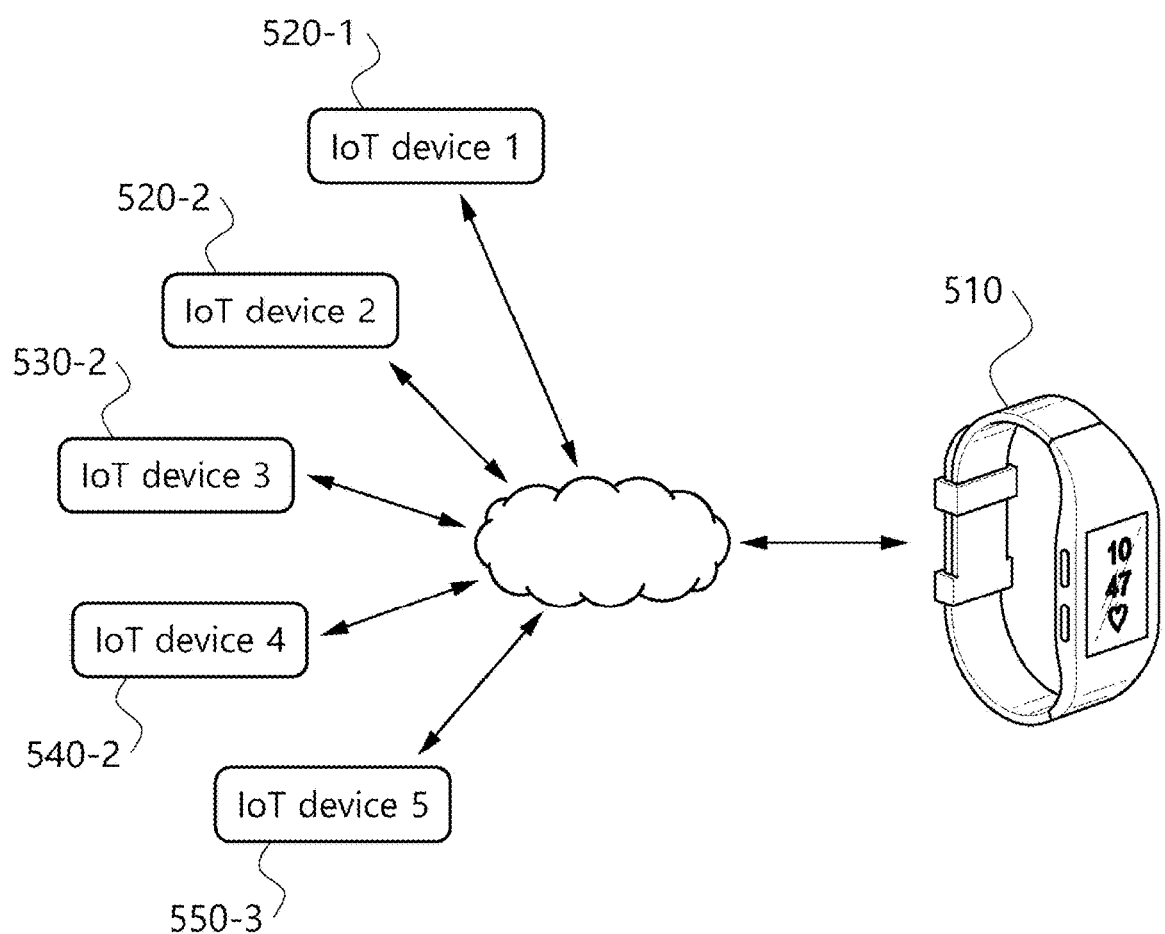
FIG. 5 is a diagram showing a method for measuring biometric information by an IoT device and a wearable device according to an embodiment of the present disclosure.

FIG. 5 is a diagram showing a method for measuring biometric information by the IoT device and the wearable device according to an embodiment of the present disclosure.

For example, as described above, the biometric information may be measured through the wearable device. However, for example, the biometric information measured using only the wearable device may have limitations. For example, when sleep information is measured through the wearable device, surrounding sleep environment information may be further necessary. For example, the ambient temperature in a sleep environment of a wearer of the wearable device may be high or low. In a specific example, sleep information measured through the wearable device in high and constant temperature environments may be used differently from sleep information measured through the wearable device in low and irregular temperature environments.

In another example, since the biometric information measured through the wearable device is detected through the acceleration sensor, the motion sensor and any other sensor for sensing physical changes, there is limited information measurement. For example, there may be limitations in acquiring information about whether the wearable device wearer has regular meals or lives a regular life.

Additionally, there may be limitations in acquiring the wearer's other information. Considering the above description, the biometric information may be measured further using an IoT device. For example, referring to FIG. 5, the wearable device 510 may communicate with IoT devices 520-1, 520-2, 520-3, 520-4, 520-5 via a communication network, and acquire information therefrom. In this instance, for example, the IoT devices 520-1, 520-2, 520-3, 520-4, 520-5 may be devices that exist in different environmental conditions.

For example, the first IoT device 520-1 may be a device installed indoors to acquire information about temperature, humidity and illuminance in a room in which a user sleeps and any other indoor condition. In another example, the second IoT device 520-2 may be a device that acquires condition information of a company in which the user works or any other space.

For example, the condition information may be air pollution level, temperature, humidity and any other surrounding environment information. That is, each of various IoT devices 520-1, 520-2, 520-3, 520-4, 520-5 may exist in different environments, and measure different information based on different conditions for each device. In a specific example, the first IoT device 520-1 may be installed indoors to measure surrounding environment information while the user is sleeping. In this instance, the wearable device 510 may acquire further detailed biometric information by measuring information about the user's sleep and acquiring the surrounding environment information from the first IoT device 520-1. In another example, the second IoT device 520-2 may be installed in the user's workplace to provide information about the user's working environment. For example, whether the user holds the same position for a long time or make movements may be measured through the wearable device 510. In this instance, the second IoT device 520-2 may measure and provide surrounding environment information when the user's information is measured, thereby acquiring further detailed biometric information.

In another example, each of the IoT devices 520-1, 520-2, 520-3, 520-4, 520-5 may provide independent information. For example, the IoT device installed indoors may measure the user's start and end times of workday via connection to the wearable device 510 and provide information to the server. That is, the IoT devices 520-1, 520-2, 520-3, 520-4, 520-5 may measure information according to each condition and transmit the information to the server.

When the dementia risk factor is derived through the above description, it is possible to acquire more precise information, and get information for deriving a new dementia risk factor.

Figure 6:
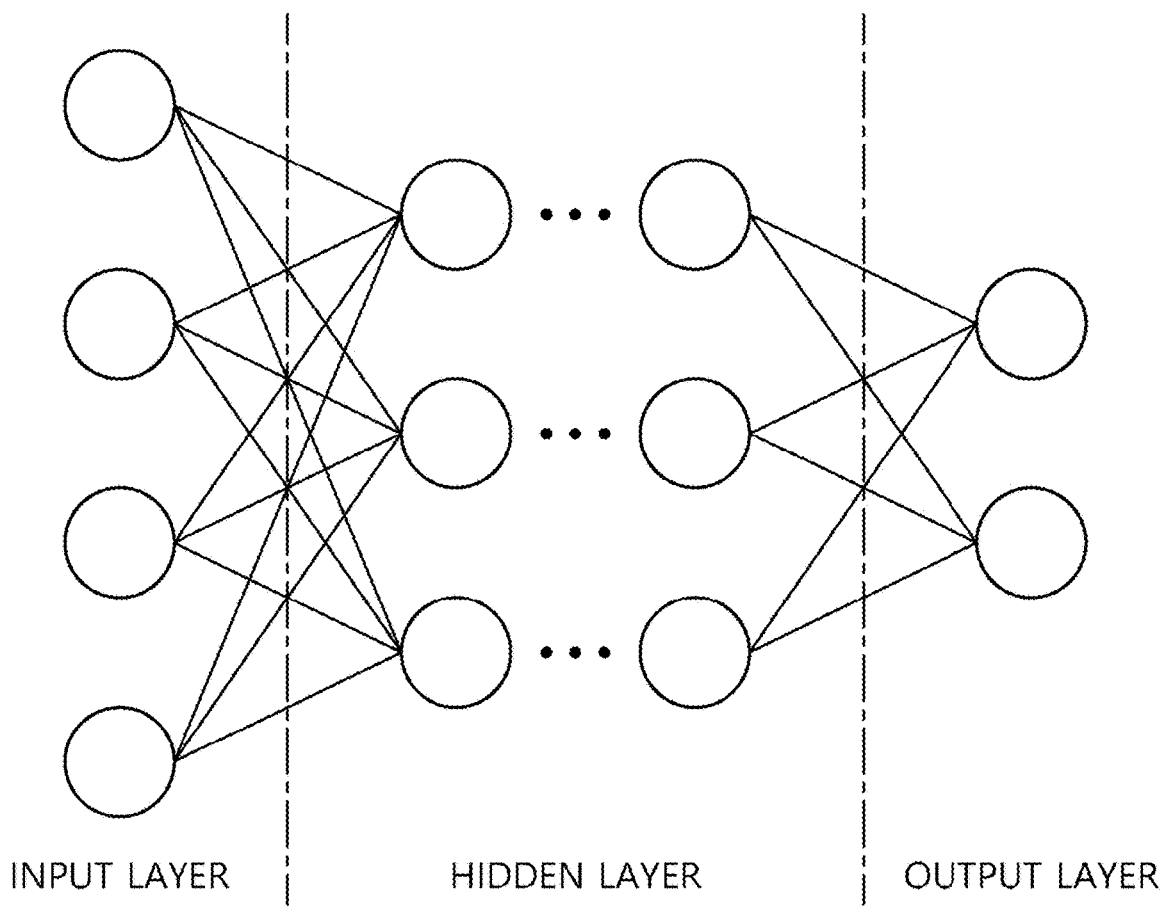
FIG. 6 is a diagram showing a method for performing deep learning according to an embodiment of the present disclosure.

FIG. 6 is a diagram showing a method for performing deep learning according to an embodiment of the present disclosure. The deep learning may refer to training a deep neural network based on a learning model. For example, referring to FIG. 6, the deep neural network may include an input layer, a plurality of hidden layers and an output layer. That is, the deep neural network may refer to an artificial neural network including a plurality of hidden layers.

In this instance, the hidden layer may provide output information to the output layer based on information trained based on input information. Additionally, the hidden layer may store a lot of information related to the input layer and the output layer, and calculate matched data based on the information.

Additionally, the learning model may store information of the input layer and information of the output layer, and may be kept trained using the information as data for training. In a specific example, the training method of deep learning may include supervised learning and unsupervised learning. In this instance, for example, the supervised learning may train the model based on preset outputs to inputs. Additionally, the unsupervised learning may determine the output layer that matches the input layer based on a variety of pattern information, not the preset outputs.

For example, the present disclosure may construct the learning model based on at least one of supervised learning or unsupervised learning, and perform matching based on it.

Additionally, for example, input information for deriving a dementia risk factor may be biometric information and measurement information, and it will be described below. Additionally, for example, input information for deriving a new dementia risk factor may be the existing dementia risk factor information and related factor information, and it will be described below.

Additionally, for example, the hidden layer may include information for determining similarity of the input layer information. In this instance, output information may be derived according to the similarity, and a new dementia risk factor may be derived as described above.

Figure 7:
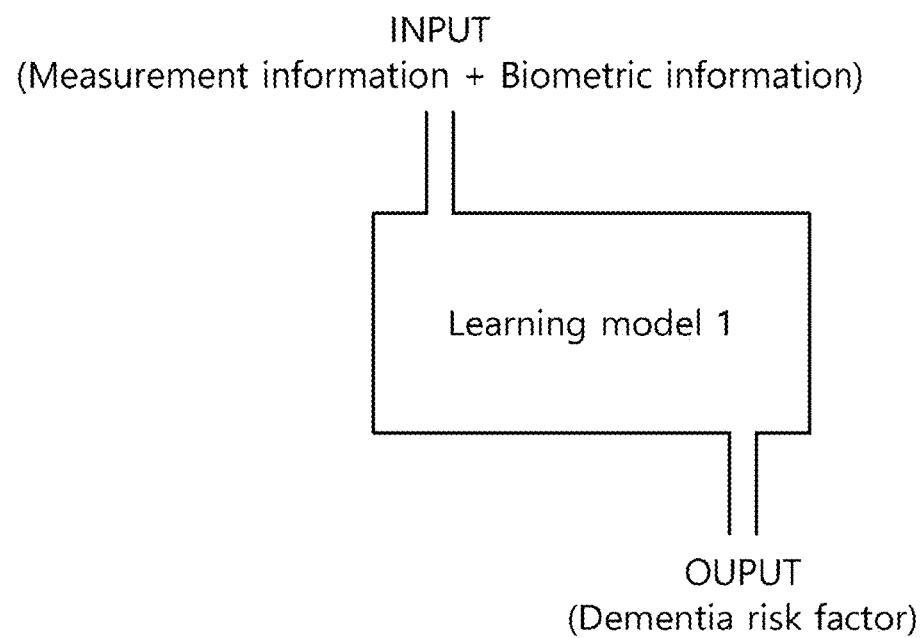
FIG. 7 is a diagram showing a method for performing deep learning according to an embodiment of the present disclosure.

FIG. 7 is a diagram showing a method for performing deep learning according to an embodiment of the present disclosure. Referring to FIG. 7, the server may include the above-described deep learning training unit.

For example, the deep learning training unit may operate based on a learning model, and the learning model may be a learning model using at least one of supervised learning or unsupervised learning as described above. Additionally, the learning model may be trained based on input information, and through this, may be kept updated. In this instance, for example, the input information for deep learning may be measurement information and biometric information. For example, as described above, the dementia risk factor may be determined by a person (e.g. a medical staff) based on the measurement information and the biometric information and inputted to a device.

In another example, the dementia risk factor may be derived via deep learning based on measurement information and biometric information. For example, the measurement information may be at least one of the above-described brain imaging, CT, MRI, EEG or medical findings data. That is, the measurement information may be measurement information through hospitals or other medical institutions. In this instance, for example, the input information may be stage information about the presence or absence of dementia or the likelihood of developing dementia based on the above-described measurement information. In another example, the measurement information as measured information itself may be input information. For example, dementia severity may be compared based on the measurement information. Additionally, the input information may include biometric information. Subsequently, deep learning may be performed through the learning model based on the above-described input information.

In this instance, the output information via deep learning may be dementia risk factor information. In this instance, the dementia risk factor information may refer to a factor that affects the development of dementia. For example, biometric information of persons determined to have a high risk for dementia through the measurement information may be used to train via deep learning.

In a more specific example, among the sleep duration, the walking distance and the number of steps data, the sleep duration may be determined as the risk factor by comparing the above-described information via deep learning. That is, the dementia risk factor information as the output information may be derived as the sleep duration. That is, the information that affects the development of dementia may be derived as the dementia risk factor via deep learning based on the measurement information and the biometric information.

Figure 8A:
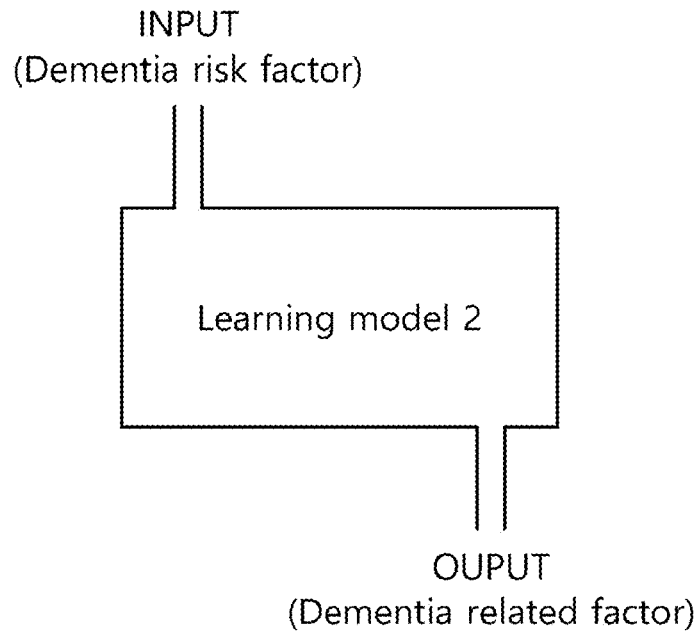
FIG. 8A is a diagram showing a method for performing deep learning according to an embodiment of the present disclosure.
Figure 8B:
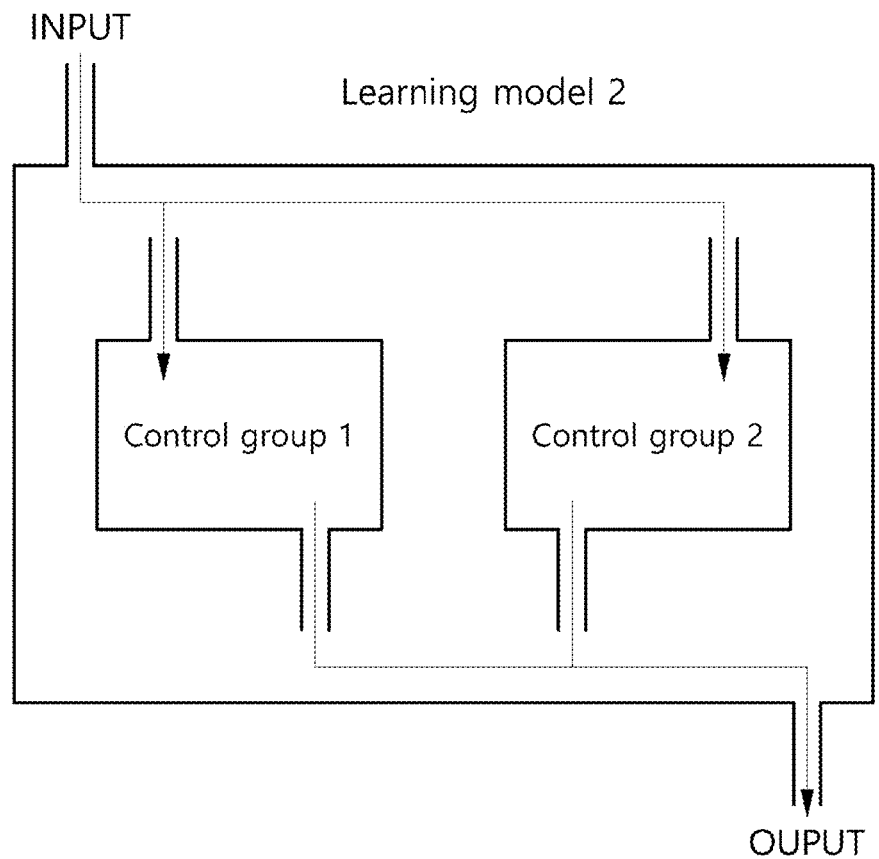
FIG. 8B is a diagram showing a method for performing deep learning according to an embodiment of the present disclosure.

FIGS. 8A and 8B are diagrams showing a method for performing deep learning according to an embodiment of the present disclosure.

Additionally, for example, referring to FIG. 8A, a new dementia risk factor may be derived via deep learning through the dementia risk factor. For example, input information in deep learning may be the dementia risk factor and biometric information related to the dementia risk factor. In a more specific example, when the sleep duration is derived as the dementia risk factor in FIG. 7 as described above, biometric information related to sleep included in the sleep duration such as sleep patterns (rapid eye movement (REM) sleep, deep sleep, light sleep) may be set as the input information.

That is, the input information may be the dementia risk factor and the biometric information related to the dementia risk factor. In this instance, for example, the new dementia risk factor may be derived based on the above-described dementia risk factor through the learning model of deep learning. For example, when the sleep duration is derived as the dementia risk factor, the presence or absence of REM sleep may be derived as the new dementia risk factor related to the dementia risk factor via deep learning. That is, the new dementia risk factor may be derived from the existing dementia risk factor.

Meanwhile, in a specific example, referring to FIG. 8B, the learning model for deriving the new dementia risk factor from the existing dementia risk factor may set control group information for comparison.

In a specific example, the learning model may set information about control group 1 with high likelihood of developing dementia and control group 2 with low likelihood of developing dementia. Additionally, for example, the learning model may set the control group through any other method, and is not limited to the above-described embodiment.

In this instance, the learning model may use the dementia risk factor and the biometric information as input information for each control group. In this instance, for example, the control group may be set as the above-described first stage in which people are categorized as normal with very low likelihood of developing dementia and are likely to develop dementia.

That is, the control group may be set as a control group corresponding to the normal category and a control group determined as subjective cognitive impairment, and they may be compared with each other.

In another example, the control group may be set as the first stage and the second stage as the above-described dementia stage. That is, groups with different dementia severities may be set as the control groups, and are not limited to the above-described embodiment. Subsequently, the learning model may compare output information acquired through each control group, and through this, derive a final dementia risk factor.

In this instance, for example, when the output information may indicate the likelihood of developing dementia based on the information between the control groups, the new dementia risk factor may be derived. Additionally, the learning model may store the above-described information, set various control groups by continuously updating, and update detailed information of the control groups to use it to derive the new dementia risk factor. That is, the new dementia risk factor may be derived via deep learning through the existing dementia risk factor and the biometric information.

Figure 9:
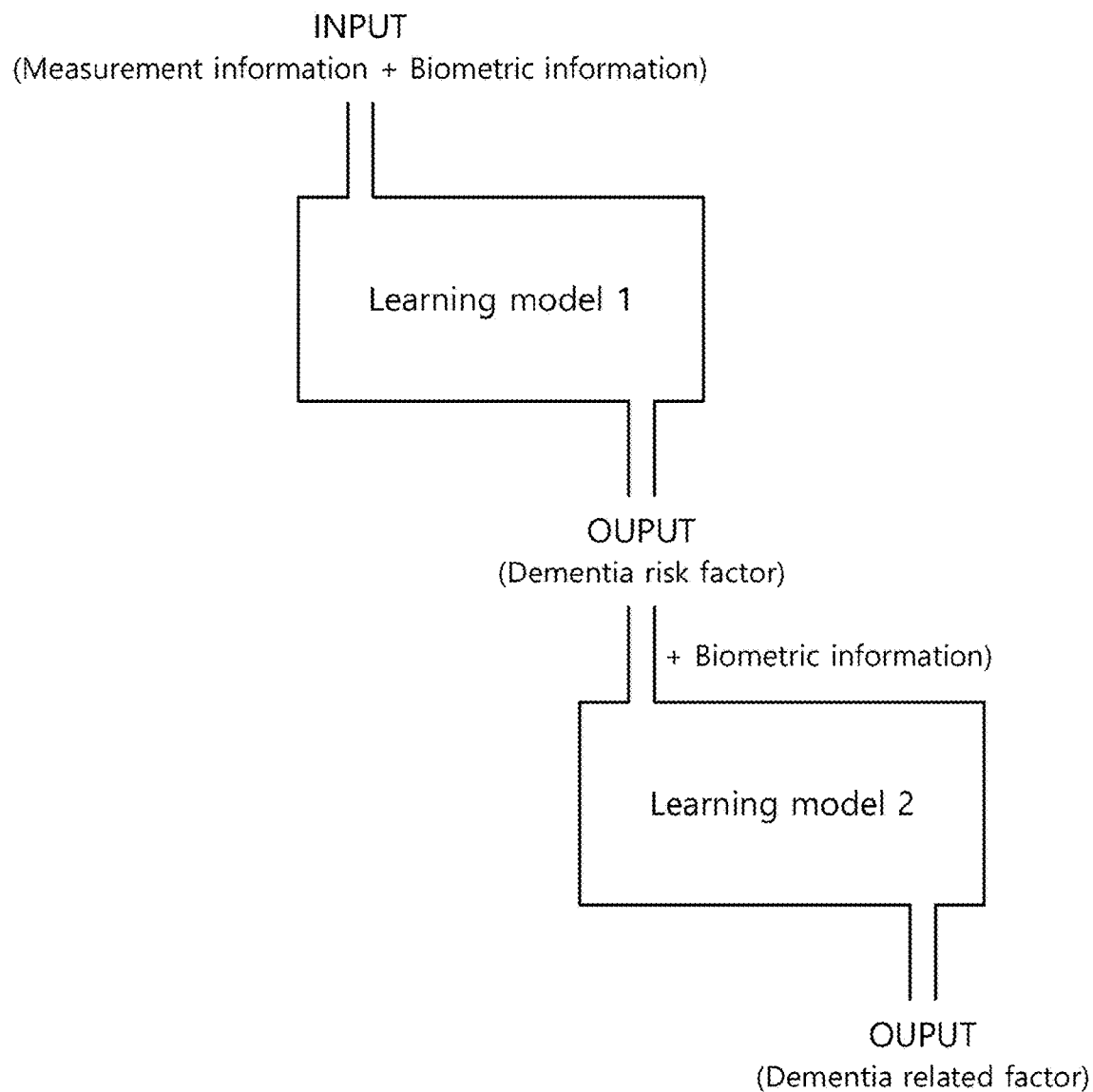
FIG. 9 is a diagram showing a method for performing deep learning according to an embodiment of the present disclosure.

FIG. 9 is a diagram showing a method for performing deep learning according to an embodiment of the present disclosure.

Referring to FIG. 9, two-step deep learning may be applied. For example, deep learning performed based on learning model 1 may derive the dementia risk factor through the measurement information and the biometric information. That is, the dementia risk factor may be derived through the above-described method of FIG. 7. In this instance, for example, the output information derived through FIG. 7 as described above may be input information for learning model 2. That is, the derived dementia risk factor may be new input information. In this instance, learning model 2 may derive the dementia risk factor with an addition of the biometric information as the input information. That is, the new dementia risk factor may be derived from the existing dementia risk factor as shown in FIGS. 8A and 8B described above, and through this, the risk factor related to dementia may be derived. That is, when deriving the dementia risk factor, two-step deep learning may be applied, and a more precise dementia risk factor may be derived through the above description.

Meanwhile, for example, the biometric information used in FIGS. 7 to 9 may include the information acquired through the IoT device in FIG. 5 as described above. That is, the information acquired further considering the biometric information acquired through the wearable device and the IoT device may be the input information used in FIGS. 7 to 9, and is not limited to the above-described embodiment.

Figure 10:
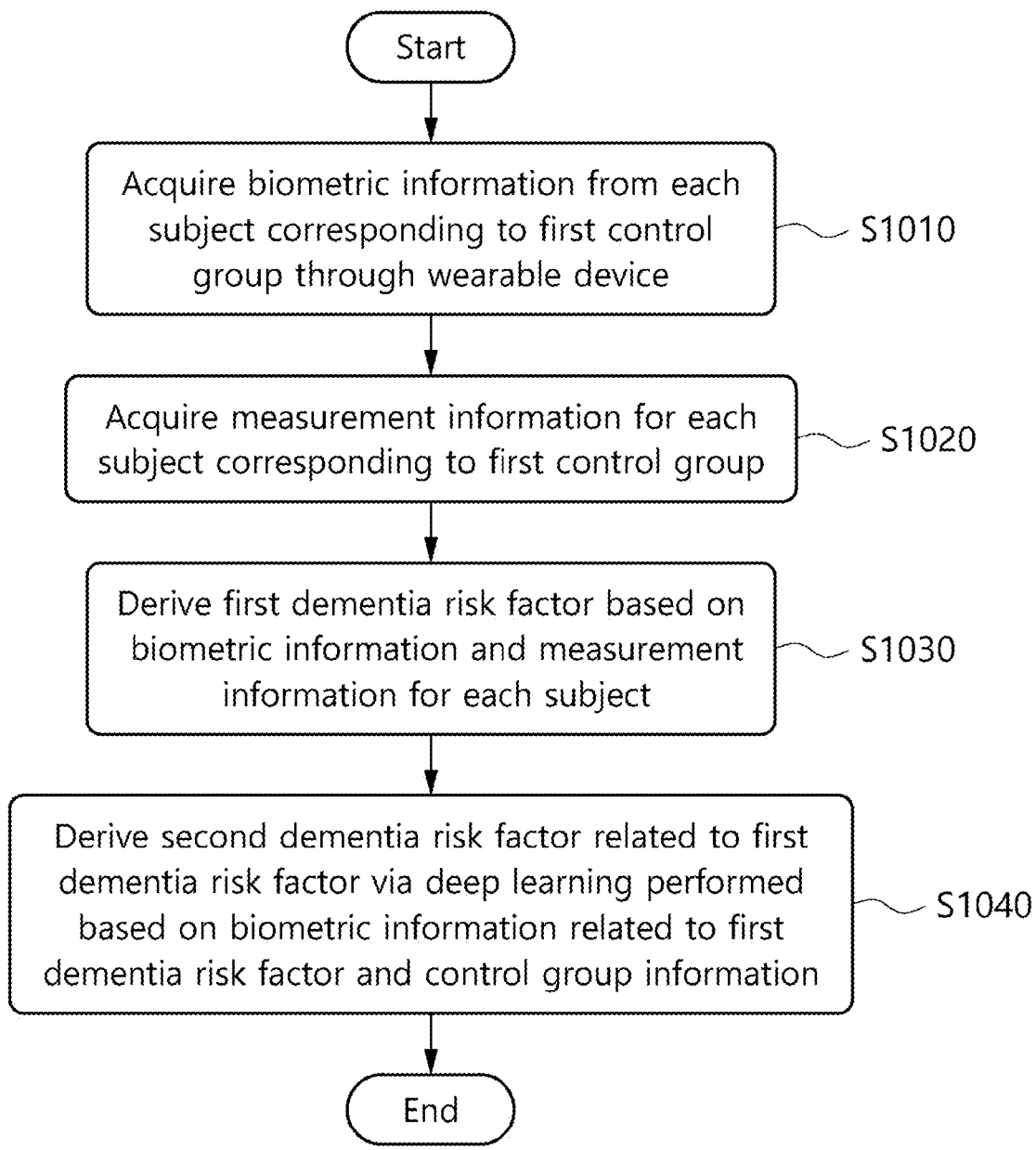
FIG. 10 is a flowchart of a method for deriving dementia risk factors according to an embodiment of the present disclosure.

FIG. 10 is a flowchart of a method for deriving dementia risk factors according to an embodiment of the present disclosure.

Referring to FIG. 10, the server may acquire biometric information from each subject corresponding to a first control group through the wearable device (S1010). In this instance, for example, in FIG. 10, the first control group may be subjects corresponding to subjective cognitive impairment state. In another example, the first control group may be a different control group according to dementia severity, and is not limited to the above-described embodiment. In this instance, the biometric information for each subject corresponding to the first control group may be acquired from the wearable device. Additionally, for example, the server may acquire measurement information for each subject corresponding to the first control group (S1020). In this instance, the measurement information may be at least one of brain imaging, CT, MRI, EEG or medical findings data information. Additionally, for example, the measurement information may refer to measurement made by medical institutions to determine the presence or absence of dementia and dementia severity, and is not limited to the above-described embodiment. In this instance, for example, the server may acquire the measurement information for each subject corresponding to the above-described first control group. Subsequently, the server may derive a first dementia risk factor based on the biometric information and the measurement information for each subject (S1030). In this instance, for example, the server may transmit the biometric information and the measurement information to medical institutions or medical staffs, and derive the first dementia risk factor based on information acquired from them. That is, the first dementia risk factor may be determined through the medical institutions or medical staffs. For example, the dementia risk factor may refer to a derived factor that may affect dementia such as calories consumed, the time spent on activities, sleep duration, the type of sleep for each sleep time, the heart rate, the number of steps, the walking distance and the number of exercises based on the measurement information corresponding to the control group as described above. That is, the dementia risk factor may be a factor that affects the development of dementia, and may be derived by the medical institutions or medical staffs.

In another example, the first dementia risk factor may be derived via deep learning of the server. That is, the server may directly derive the first dementia risk factor information via deep learning based on the acquired information without transmitting the biometric information and the measurement information to the medical institution or medical staff. For example, the measurement information and the biometric information for the control group may be matched via deep learning, and through this, the first dementia risk factor information may be derived.

Subsequently, a second dementia risk factor related to the first dementia risk factor may be derived via deep learning performed based on the biometric information related to the first dementia risk factor and the control group information (S1040). In this instance, for example, for the control group, in addition to the above-described first control group, a second control group may be set. For example, in FIG. 10, the second control group may be a control group corresponding to normal state. That is, the first control group may be a control group corresponding to subjective cognitive impairment state, and the second control group may be a control group corresponding to normal state. Additionally, for example, the control group may be variously set, and the above-described method may be an example. In this instance, for example, the biometric information of the subjects corresponding to the first control group and the subjects corresponding to the second control group may be measured through the wearable device. The server may perform the above-described deep learning based on the above-described measurement information and the control group feature information. Subsequently, the second dementia risk factor may be derived from the biometric information related to the first dementia risk factor. That is, the second dementia risk factor may be a new dementia risk factor derived from the first dementia risk factor. That is, as described above, the server may derive the new dementia risk factor via deep learning through the existing dementia risk factor, the biometric information and the control group information.

The above-described embodiments of the present disclosure may be implemented through a variety of means. For example, the embodiments of the present disclosure may be implemented by hardware, firmware, software or a combination thereof.

In the case of implementation by hardware, the method according to embodiments of the present disclosure may be implemented by one or more Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro controllers and micro processors.

In the case of implementation by firmware or software, the method according to embodiments of the present disclosure may be implemented in the form of modules, procedures or functions that perform the above-described functions or operations. The software code may be stored in a memory unit and executed by the processor. The memory unit may be disposed inside or outside of the processor to send and receive data to/from the processor by a variety of well-known means.

The detailed description of the preferred embodiments of the present disclosure as disclosed above is provided to allow those skilled in the art to implement and practice the present disclosure. Although the present disclosure has been hereinabove described with reference to the preferred embodiments of the present disclosure, those skilled in the art will understand that various modifications and changes may be made to the present disclosure without departing from the spirit and scope of the present disclosure set forth in the appended claims. Accordingly, the present disclosure is not limited to the disclosed embodiments and is intended to provide the broadest scope that is consistent with the disclosed principles and new features. Additionally, although the preferred embodiments of the present disclosure have been hereinabove illustrated and described, the present disclosure is not limited to the above-described particular embodiments, and a variety of modifications may be made thereto by those having ordinary skill in the technical field pertaining to the present disclosure without departing from the claimed subject matter of the present disclosure in the appended claims, and such modifications should not be individually understood from the spirit or scope of the present disclosure.

Additionally, the present disclosure describes the product invention and the method invention, and the descriptions of the two inventions may be complementarily applied where necessary.

The invention claimed is:

1. A system for determining dementia risk factors, comprising:
a server comprising an artificial neural network (ANN), a transmitter of the server, a receiver of the server, a processor of the server, a memory of the server communicatively coupled to the processor of the server and storing instructions operable when executed by the processor of the server to perform a predetermined function and automatically determining the dementia risk factors with a biometric information and a dementia related information, wherein
the dementia related information comprises a first dementia related information, a second dementia related information, a third dementia related information and a fourth dementia related information, and
the ANN is implemented as an application specific integrated circuit (ASIC);
a wearable device comprising a transmitter of the wearable device, a receiver of the wearable device, an acceleration sensor, a motion sensor, a processor of the wearable device, a memory of the wearable device communicatively coupled to the processor of the wearable device and storing instructions operable when executed by the processor of the wearable device to perform a predetermined function, automatically measuring the biometric information including consumed calories, a spent activity time, a sleep duration, a type of sleep for each sleep time, a heart rate, a number of steps, a walking distance and a number of exercises and communicating with a plurality of Internet of Things (IoT) devices;
the plurality of Internet of Things (IoT) devices, each of the plurality of IoT devices comprising a processor of the IoT devices, a memory of the IoT devices communicatively coupled to the processor of the IoT devices and storing instructions operable when executed by the processor of the IoT devices to perform a predetermined function, a transmitter and a receiver and automatically communicate with the server and the wearable device, wherein:
the plurality of IoT devices comprises a first IoT device, a second IoT device and a third IoT device;
the first IoT device is a device that is fixed at a predetermined location, operated based on a IoT cloud, automatically receives a signal from the wearable device and transmits data to the server and the second and third IoT devices through the IoT cloud;
the second IoT device is a device with a power of a predetermined level which is lower than a power of the first and third IoT devices; and
the third IoT device is a device that is installed in an indoor space and automatically measures a temperature, a humidity, an air pollution level and an illuminance of an indoor environment of a wearer of the wearable device, wherein the third IoT device further automatically measures an information of a start time and an end time of a workday and the sleep duration of the wearer of the wearable device via a connection to the wearable device and automatically transmits the information of the start time and the end time to the server;
a computed tomography (CT) scanner measuring the first dementia related information;
a magnetic resonance imaging (MRI) scanner measuring the second dementia related information;
an electroencephalogram (EEG) recorder measuring the third dementia related information;
an amyloid positron emission tomography (PET) scanner measuring a fourth dementia related information; and
a blood biomarker measuring the fifth dementia related information.

* * * * *